United States Patent
Li et al.

(10) Patent No.: US 10,004,271 B2
(45) Date of Patent: Jun. 26, 2018

(54) ATOMIZER AND ELECTRONIC SMOKING DEVICE HAVING SAME

(71) Applicant: Shenzhen First Union Technology Co., Ltd., Shenzhen, Guangdong Province (CN)

(72) Inventors: Yonghai Li, Shenzhen (CN); Zhongli Xu, Shenzhen (CN); Shuyun Hu, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 0 days. days.

(21) Appl. No.: 15/390,480

(22) Filed: Dec. 24, 2016

(65) Prior Publication Data

US 2017/0105453 A1    Apr. 20, 2017

(30) Foreign Application Priority Data

Dec. 25, 2015  (CN) .......................... 2015 1 0985835

(51) Int. Cl.
  A24F 47/00    (2006.01)
(52) U.S. Cl.
  CPC .................................. *A24F 47/008* (2013.01)

(58) Field of Classification Search
  CPC .... A24F 47/008; A24F 47/004; A24F 47/002; A24F 7/02; F16J 15/022; H05B 6/36; H05B 6/362; H05B 6/108; F22B 1/284; F16K 15/025
  USPC ............. 131/329, 194, 271, 273; 128/202.21
  See application file for complete search history.

(56) References Cited

U.S. PATENT DOCUMENTS

| | | | |
|---|---|---|---|
| 2014/0334803 A1* | 11/2014 | Li ............................ | H05B 3/03 392/394 |
| 2015/0250231 A1* | 9/2015 | Hon ...................... | A24F 47/008 131/329 |
| 2016/0135505 A1* | 5/2016 | Li ............................ | H05B 3/44 131/329 |

\* cited by examiner

*Primary Examiner* — Edwin A. Leon
(74) *Attorney, Agent, or Firm* — Cheng-Ju Chiang (57) ABSTRACT

An exemplary atomizer includes a housing, a conductive part at an end of the housing, a mouthpiece with an air outlet, a liquid chamber, and at least one heating element. The liquid chamber is in the housing and configured for storing tobacco liquid. The at least one heating element is electrically connected to the conductive part. The heating element includes a liquid carrier and a heating part integrally formed with the liquid carrier. The liquid carrier has a micro porous structure. The liquid carrier is in contact with the tobacco liquid. The liquid carrier is configured for absorbing the tobacco liquid, and the heating part is configured for heating the tobacco liquid to form aerosol.

10 Claims, 8 Drawing Sheets

ATOMIZER AND ELECTRONIC SMOKING DEVICE HAVING SAME

TECHNICAL FIELD

The present invention relates to electronic smoking devices, and particularly to an atomizer and an electronic smoking device using same.

BACKGROUND ART

A typical heating assembly in an atomizer includes a liquid conducting body and a heating wire wrapped around the liquid conducting body. The liquid conducting body is usually made of glass fiber core. However, this kind of heating assembly may be unsuitable for atomizers of large wattage. For example, after assembling, a gap between the heating wire and a surface of the glass fiber core may be uneven. When the heating wire heats in large wattage, the glass fiber core may be burnt due to high temperature, thus rendering user experience unsatisfactory.

What are needed, therefore, are an atomizer and an electronic smoking device using same, which can overcome the above shortcomings.

SUMMARY

An exemplary atomizer includes a housing, a conductive part at an end of the housing, a mouthpiece with an air outlet, a liquid chamber, and at least one heating element. The liquid chamber is in the housing and configured for storing tobacco liquid. The at least one heating element is electrically connected to the conductive part. The heating element includes a liquid carrier and a heating part integrally formed with the liquid carrier. The liquid carrier has a micro porous structure. The liquid carrier is in contact with the tobacco liquid. The liquid carrier is configured for absorbing the tobacco liquid, and the heating part is configured for heating the tobacco liquid to form aerosol.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Figure 1:
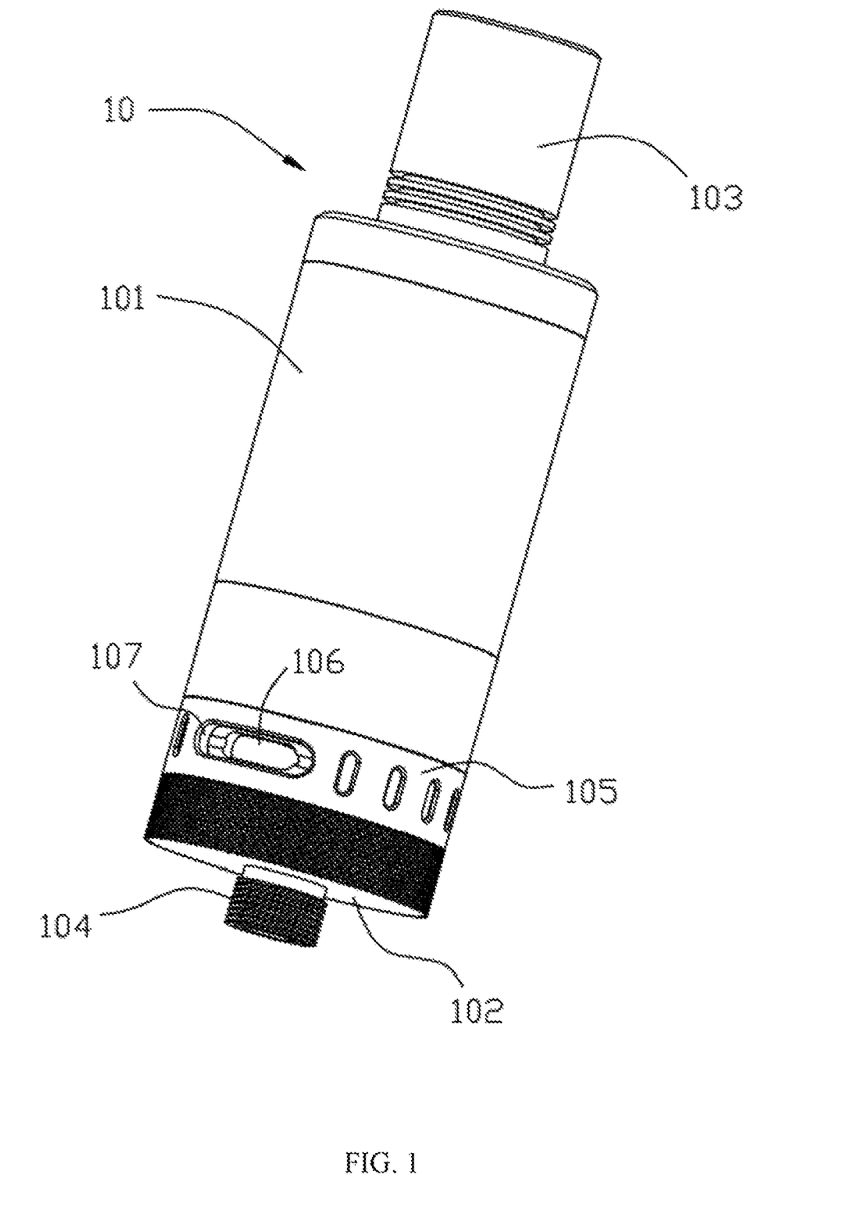
FIG. 1 is a perspective view of an atomizer according to a first embodiment.

Referring to FIG. 1, an atomizer 10 is shown. The atomizer 10 is substantially cylindrical, and includes a housing 101, and a mouthpiece 103 and a conductive part 102 arranged at two opposite ends of the housing 101. A threaded part 104 is arranged on the conductive part 102, and configured (i.e., structured and arranged) for connecting with a power supply. A liquid chamber 109 for storing tobacco liquid and a heating element 108 for heating tobacco liquid are provided in the housing 101 (described in detail later). The housing 101 defines an air inlet 106. An adjusting ring 105 with adjusting holes 107 is further provided corresponding to the air inlet 106. The adjusting ring 105 is rotatable, such that an amount of air inflow can be adjusted by changing an area that the adjusting holes 107 overlap the air inlet 106.

Figure 2:
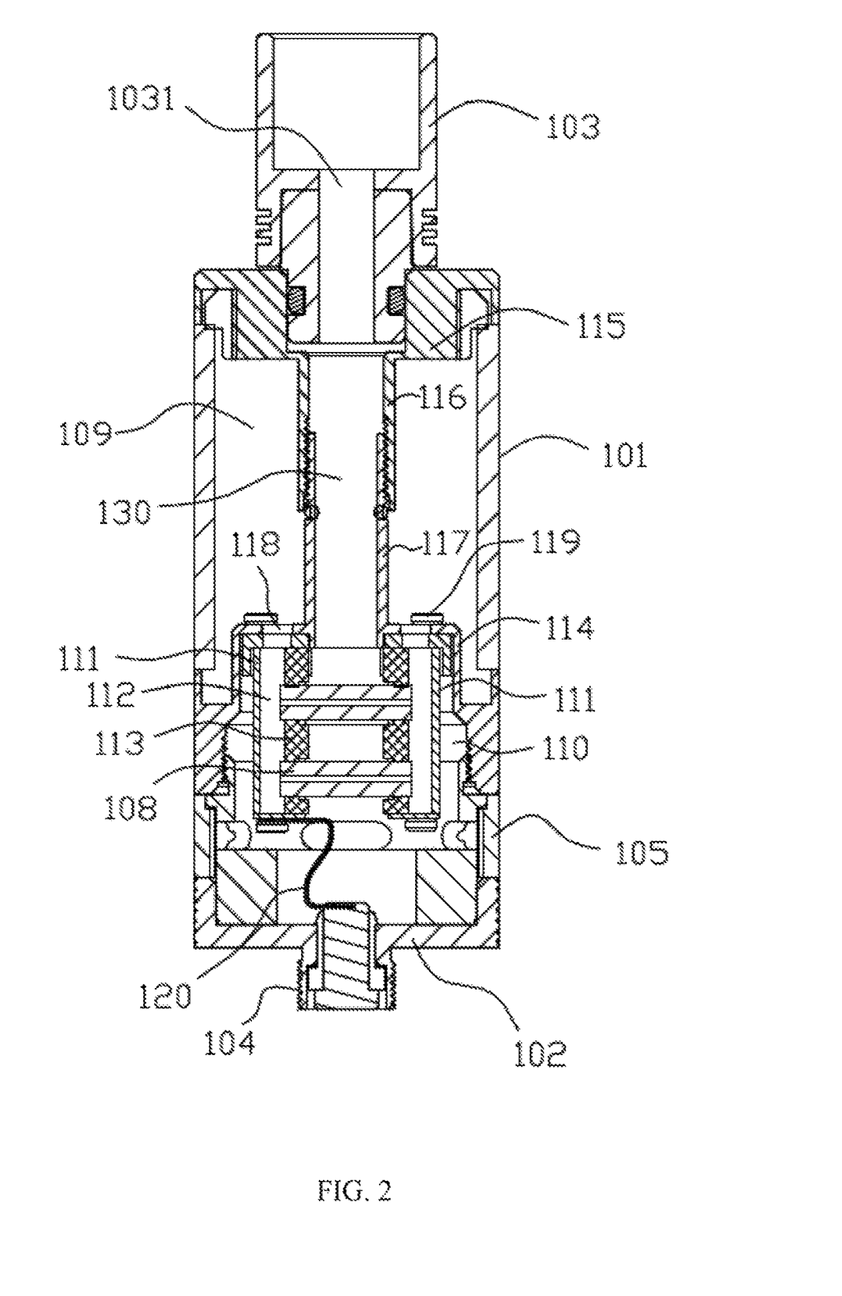
FIG. 2 is a cross-sectional view of the atomizer of FIG. 1.

Referring to FIG. 2, the housing 101 defines the liquid chamber 109. At least one heating element 108 is arranged in the housing 101, and is electrically connected with the conductive part 102. In the present embodiment, the atomizer 10 includes two heating elements 108. The heating element 108 includes a liquid carrier 1081 and heating part integrally formed with the liquid carrier 1081. The liquid carrier 1081 is in contact with tobacco liquid. The liquid carrier 1081 absorbs tobacco liquid, and conveys the tobacco liquid to the heating element 108 for atomization. The heating element 108 heats the tobacco liquid to form aerosol, and then the aerosol is expelled via an air outlet 1031 of the mouthpiece 103. The heating element 108 is integrally formed, and can absorb the tobacco liquid and heat the tobacco liquid. Accordingly, the heating element 108 has a simple structure, and it is convenient to assemble the heating element 108 into the atomizer 10.

Figure 5:
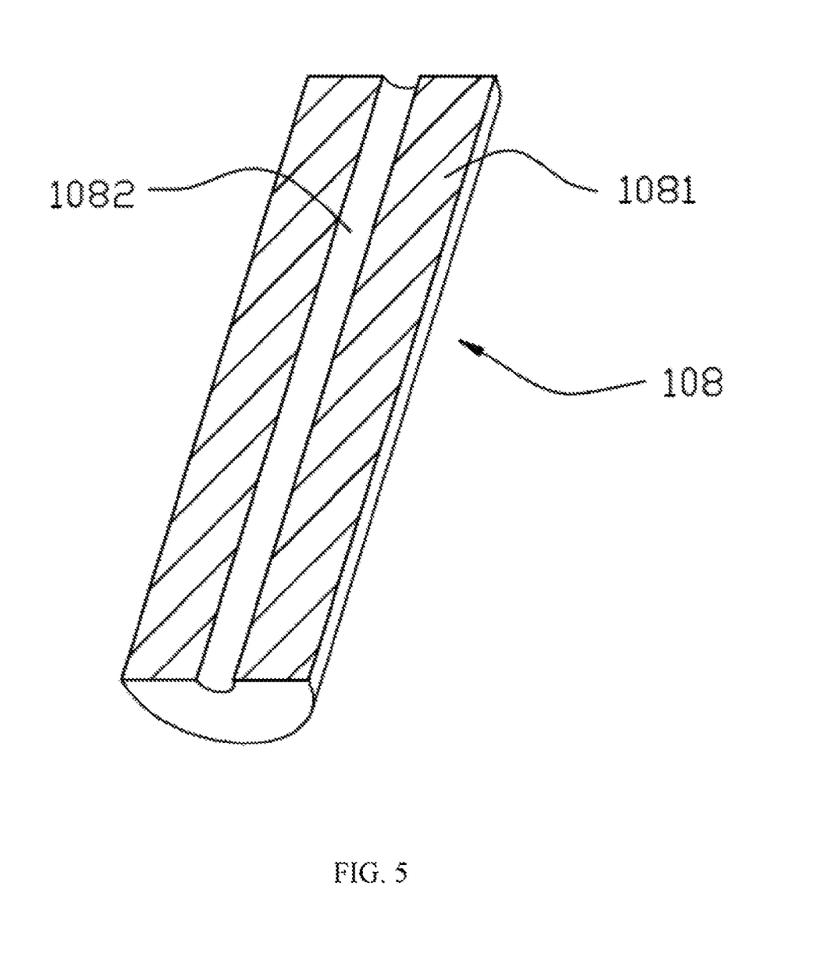
FIG. 5 is the heating element of the atomizer of FIG. 1 according to the first embodiment.

In the present embodiment, quite usefully, the heating element 108 is sintered in a high temperature by nanosized metallic powder and a material of the liquid carrier 1081, as seen in FIG. 5. The liquid carrier 1081 is made of a material selected from a group consisting of aluminum oxide, zirconium oxide, and silicone dioxide. In manufacturing, the nanosized metallic powder and agent of air bubbles are added into at least one of aluminum oxide, zirconium oxide, and silicone dioxide. Then the mixture is sintered in high temperature to form an integral structure. The aluminum oxide, zirconium oxide, or silicone dioxide forms the liquid carrier 1081 with porosity upon effect of the agent of air bubbles. The nanosized metallic powder is evenly dispersed in the liquid carrier 1081, and molecules are interconnected to form a conductor with a certain resistance. In the present embodiment, the nanosized metallic powder may be selected from a group consisting of nickel, chromium, titanium, manganese, tungsten, molybdenum, and any combination thereof. The heating element 108 can heat uniformly, is suitable for atomizer of large wattage, and can absorb tobacco liquid due to its porosity. The heating element 108 can transfer tobacco liquid from two ends to a middle part, and heat the tobacco liquid to form aerosol. Further, to increase an amount of tobacco liquid the heating element 108 conducts, and to improve heating uniformity, the heating element 108 defines a liquid conducting hole 1082 extending axially.

Referring to FIG. 2, an atomizing chamber 110 is further defined in the housing 101, and is separated from the liquid chamber 109. A liquid inlet 118 is defined between the atomizing chamber 110 and the liquid chamber 109. The air outlet 1031 is in communication with the atomizing chamber 110. The heating element 108 is received in the atomizing chamber 110. The atomizing chamber 110 is positioned below the liquid chamber 109. The tobacco liquid flows out from the liquid inlet 118 and is then absorbed by the heating element 108.

Figure 3:
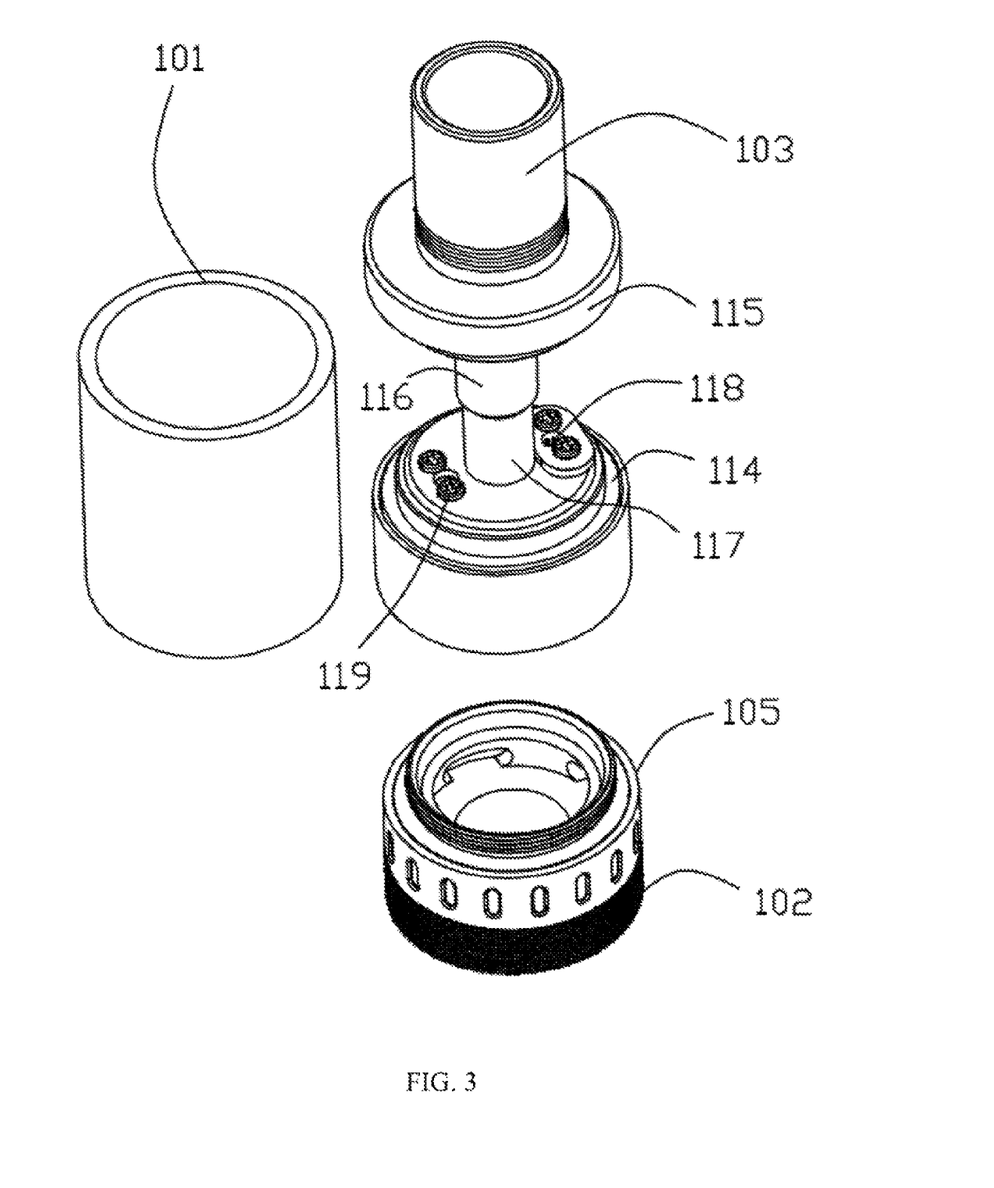
FIG. 3 is an exploded perspective view of the atomizer of FIG. 1.

Referring to FIGS. 2-3, a top isolation cover 115 and a bottom isolation cover 114 are further provided in housing 101. The top isolation cover 115 is configured for connecting to the mouthpiece 103. The bottom isolation cover 114 is configured for isolating the atomizing chamber 110 from the liquid chamber 109. The top isolation cover 115 and the bottom isolation cover 114 each include a tubular part 116 or 117. The tubular parts 116, 117 are interconnected to form an air passage 130 connecting the air outlet 1031 and the atomizing chamber 110. In the present embodiment, the tubular parts 116, 117 are coupled by screw threads, and by a sealing ring. The conductive part 102 and the sealing ring 105 are detachably connected with a lower part of the bottom isolation cover 114. The conductive part 102, the sealing ring 105 and the bottom isolation cover 114 cooperatively define the atomizing chamber 110. The top isolation cover 115, the bottom isolation cover 114, and the housing 101 cooperatively define an annular space, served as the liquid chamber 109. The liquid inlet 118 is defined in the bottom isolation cover 114. In the present embodiment, two liquid inlets 118 are defined in the bottom isolation cover 114.

Two metallic brackets 111 are further detachably provided in the atomizing chamber 110. The two metallic brackets 111 are configured for fixing the heating elements 108. The heating elements 108 are spaced apart from each other. The metallic bracket 111 defines liquid grooves 112 in alignment with the liquid inlet 118. Two opposite ends of the heating element 108 are in contact with the metallic bracket 111, and are positioned in the liquid grooves 112. In assembly, the metallic bracket 111 and the heating elements 108 as a whole are fixed on the bottom isolation cover 114 via screws 119. Two opposite ends of the heating elements 108 extend into the liquid grooves 112 to absorb tobacco liquid. Two opposite ends of the heating elements 108 contact with the two metallic brackets 111, respectively. The two metallic brackets 111 are both electrically conductive, and each is connected to a positive electrode and a negative electrode of the conductive part 102. Quite usefully, the metallic brackets 111 are connected with the conductive part 102 via electrically conductive flat springs 120 (only one of them shown in the drawings). The electrically conductive flat springs 120 are fixed at a bottom part of the metallic brackets 111.

Figure 4:
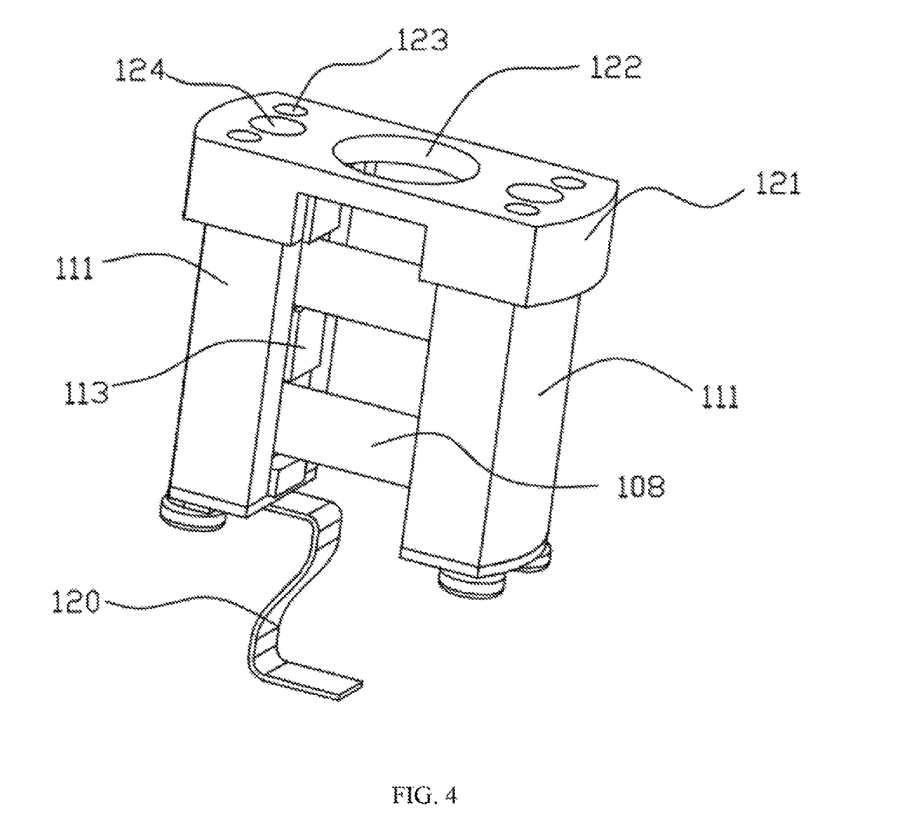
FIG. 4 is an assembled perspective view of a heating element and metallic brackets in the atomizer of FIG. 1.

Referring to FIG. 4, the two heating elements 108 are bridged between the two metallic brackets 111, and are separated by a silicone holder 113. Top ends of the metallic brackets 111 are fixedly connected by a cap 121. The cap 121 defines an air hole 122 at a central part, which is spatially corresponding to the tubular part 117. Accordingly, aerosol can enter the air passage 130. The cap 121 further defines through holes 124 in communication with the liquid inlet 118 and the liquid groove 112. The heating elements 108, the metallic holder 111, and the cap 121 are assembled as a heating assembly. The heating assembly can be assembled on the bottom isolation cover 114 conveniently. The caps 121 further define a plurality of screw holes 123 for assembling. The conductive part 102 is threadedly coupled to the bottom isolation cover 114. After removing the conductive part 102, the whole heating assembly can be replaced easily.

Figure 6:
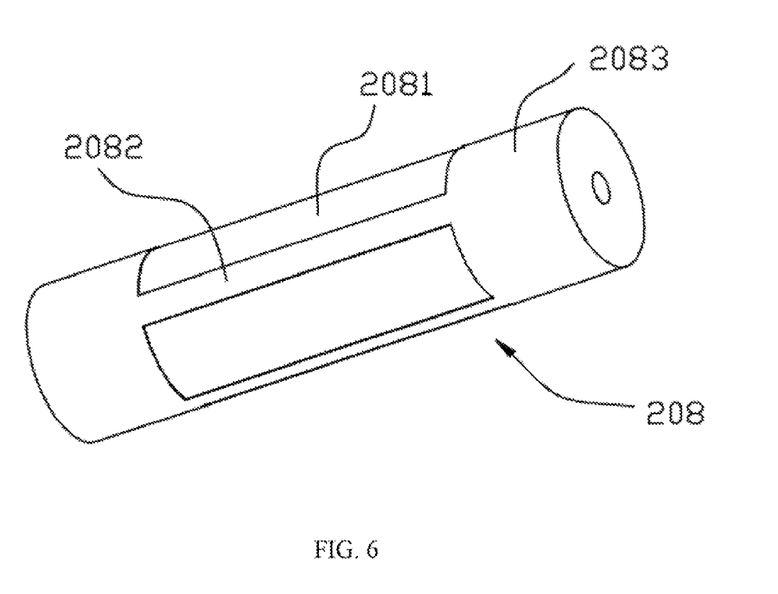
FIG. 6 is a heating element according to a second embodiment.

Referring to FIG. 6, a heating element 208, according to another embodiment, is shown. The heating element 208 can replace the heating element 108 of the first embodiment. The heating element 208 includes a liquid carrier 2081 and a metallic heating layer 2082 printed on at least one part of a surface of the liquid carrier 2081. Quite usefully, the liquid carrier 2081 is made of micro porous ceramic. Metallic resistance material slurry is printed on a surface of the micro porous ceramic using printing technology of circuit, and then the metallic material and the micro porous ceramic are together sintered. It is to be understood that the liquid carrier 2081 may be formed by sintering a mixture of agent of air bubbles and any of aluminum oxide, zirconium oxide, and silicone dioxide. Further, an electrically conductive layer 2083 is printed on the surface adjacent to two ends of the liquid carrier 2081. The electrically conductive layer 2083 is electrically connected with the metallic heating layer 2082.

Figure 7:
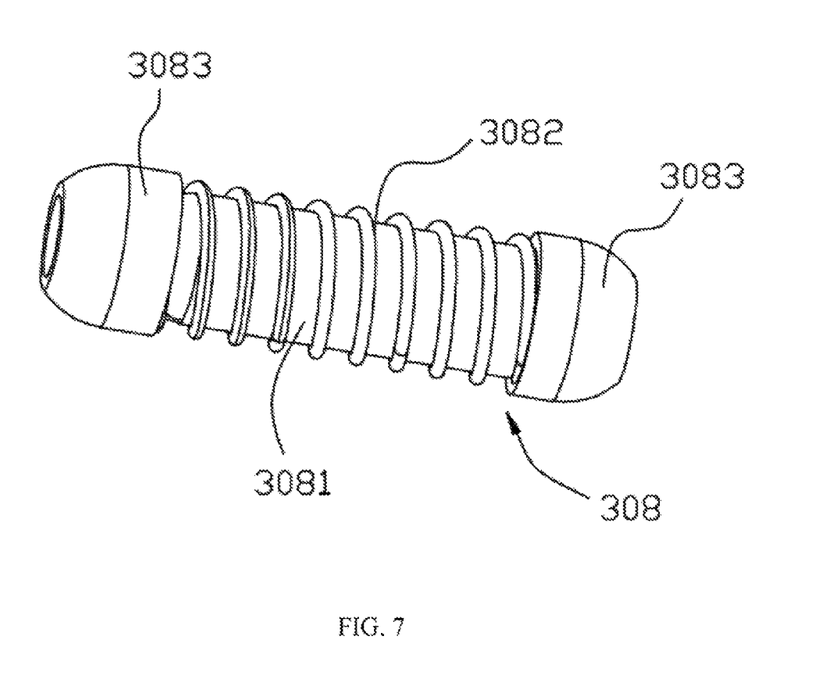
FIG. 7 is a heating element according to a third embodiment.

Referring to FIG. 7, a heating element 308 according to an alternative embodiment is shown. The heating element 308 includes a liquid carrier 3081 and a heating wire 3082 wound around the liquid carrier 3081. The heating element 308 further includes conductive caps 3083 arranged at two opposite end of the liquid carrier 3081. The conductive caps 3083 are configured for connecting with two ends of the heating wire 3082, and fixing the heating wire 3082 on the liquid carrier 3081. It is noteworthy that in other embodiments, the heating wire 3082 may instead be a heating piece. Quite usefully, the liquid carrier 2081 is made of micro porous ceramic. It is to be understood that in other embodiments, the liquid carrier 3081 may be formed by sintering an agent of air bubbles and a material selected from a group consisting of aluminum oxide, zirconium oxide, and silicone dioxide.

Figure 8:
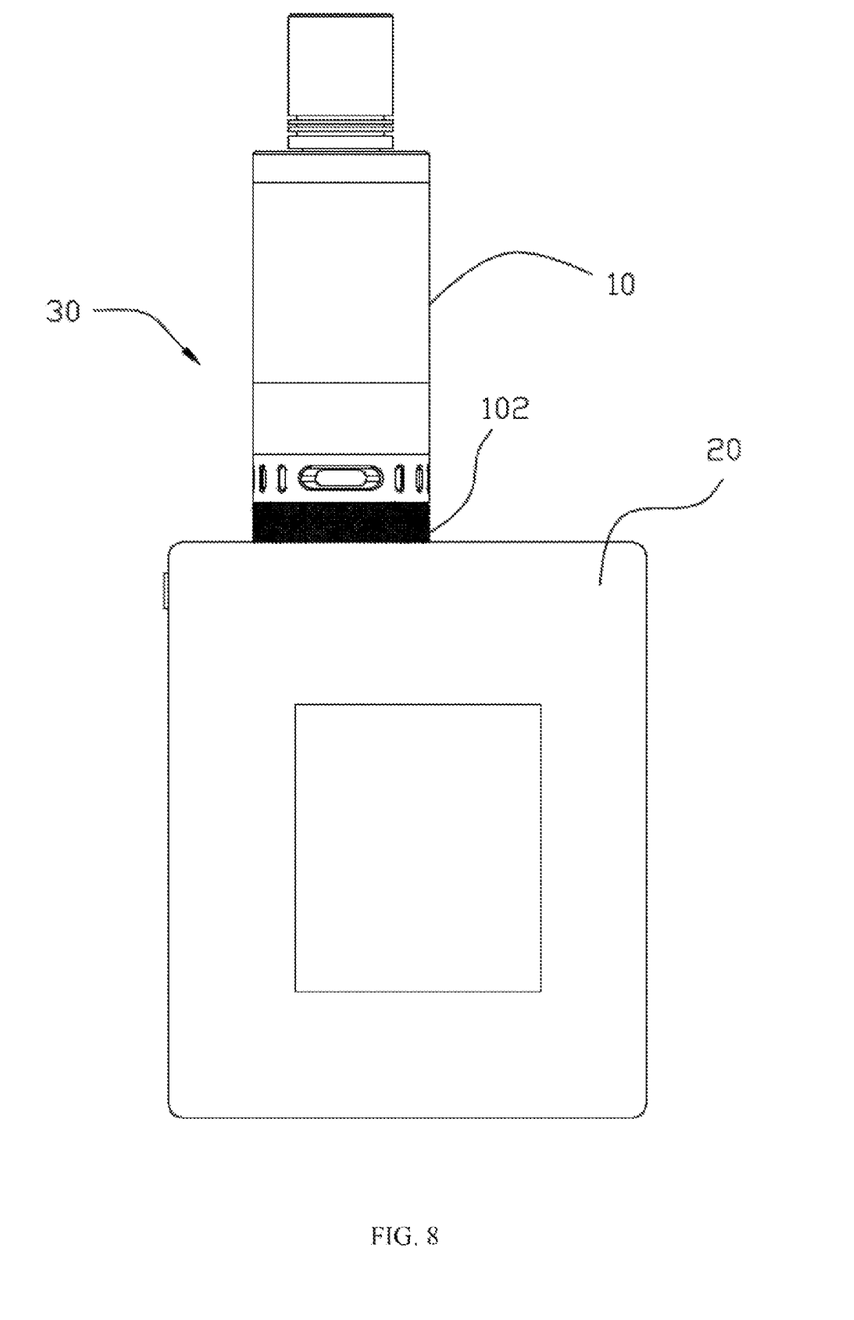
FIG. 8 is a heating element according to a fourth embodiment.

Referring to FIG. 8, an electronic smoking device 30 is shown. The electronic smoking device 30 includes the above atomizer 10 and a power supply 20. The power supply 20 is detachably connected with the atomizer 10. The conductive part 102 is configured for electrically connecting to the power supply 20. The power supply 20 includes buttons (not shown) configured for turning on/off the electronic smoking device 30, and adjusting an output wattage of the atomizer 10.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer, comprising:
a housing;
a conductive part at an end of the housing;
a mouthpiece with an air outlet;
a liquid chamber in the housing and being configured for storing tobacco liquid;
at least one heating element electrically connected to the conductive part, the heating element comprising a liquid carrier and a heating part integrally formed with the liquid carrier, the liquid carrier having a micro porous structure, the liquid carrier being in contact with the tobacco liquid, the liquid carrier being configured for absorbing the tobacco liquid, the heating part being configured for heating the tobacco liquid to form aerosol; and
an atomizing chamber in the housing, wherein the atomizing chamber is separated from the liquid chamber, the atomizer further defines a liquid inlet between the atomizing chamber and the liquid chamber; the air outlet is in communication with the atomizing chamber, and the heating element is arranged in the atomizing chamber;
wherein the atomizer further comprises two metallic brackets detachably arranged in the atomizing chamber, the metallic brackets are configured for fixing the heating element, each metallic bracket defines a liquid groove aligned with the liquid inlet, ends of the heating element are in contact with the metallic brackets, and are positioned within the liquid grooves.

2. The atomizer according to claim 1, wherein the heating element is made of an identical material, is formed by sintering nanosized metallic powder and a material of the liquid carrier in a high temperature.

3. The atomizer according to claim 2, wherein the liquid carrier is made of a material selected from a group consisting of aluminum oxide, zirconium oxide, and silicone dioxide.

4. The atomizer according to claim 1, wherein the heating part is a metallic heating layer printed on at least one part of a surface of the liquid carrier.

5. The atomizer according to claim 1, wherein the heating part is a heating wire wound around the liquid carrier, the liquid carrier comprises two opposite ends, the heating element further comprises two conductive caps arranged at two ends of the liquid carrier respectively, and the conductive caps are configured for connecting two opposite ends of the heating wire, and fixing the heating wire on the liquid carrier.

6. The atomizer according to claim 4, wherein the liquid carrier is made of micro porous ceramic.

7. The atomizer according to claim 1, wherein the metallic brackets are electrically connected with the conductive part via an electrically conductive flat spring.

8. The atomizer according to claim 1, further comprising a top isolation cover and a bottom isolation cover both arranged in the housing, wherein the top isolation cover and the bottom isolation cover each comprise a tubular part, the top isolation cover is configured for connecting the mouthpiece, the bottom isolation cover is configured for separating the liquid chamber from the atomizing chamber, and the tubular parts of the top and bottom isolation covers are interconnected to form an air passage connecting the air outlet and the atomizing chamber.

9. The atomizer according to claim 1, wherein the housing defines an air inlet, the atomizer further comprises an adjusting ring adjacent to the air inlet, the adjusting ring defines a plurality of adjusting holes corresponding to the air inlet; the adjusting ring is rotatable, such that an amount of air inflow can be adjusted by changing an area that the adjusting holes overlap the air inlet.

10. An electrically smoking device, comprising:
an atomizer according to claim 1; and
a power supply detachably connected with the atomizer, the power supply being configured for supplying the atomizer power.

* * * * *